(12) United States Patent
Dekeyser et al.

(10) Patent No.: US 6,451,835 B1
(45) Date of Patent: Sep. 17, 2002

(54) PESTICIDAL FLUOROETHYL PYRAZOLE DERIVATIVES

(75) Inventors: Mark A. Dekeyser, Waterloo (CA); Paul T. McDonald, Middlebury, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 0 days.

(21) Appl. No.: 10/007,867

(22) Filed: Nov. 13, 2001

(51) Int. Cl.$^7$ .................. A01N 43/56; C07D 231/12
(52) U.S. Cl. .................. 514/406; 548/377.1
(58) Field of Search .................. 548/377.1; 514/406

(56) References Cited

U.S. PATENT DOCUMENTS 2,547,724 A  4/1951  Sundholm

OTHER PUBLICATIONS

Lee et al, *Chemical Abstracts,* vol. 136, No. 163977, 2001.*
Baklouti and Hedhli, Journal of Fluorine Chemistry, 45:255–263 (1989), (CA112:198205).

Chemical Abstracts, JP 59053468 (1999).

* cited by examiner

*Primary Examiner*—Robert W. Ramsuer
(74) *Attorney, Agent, or Firm*—Daniel Reitenbach

(57) ABSTRACT

Disclosed herein are fluoroethyl pyrazole compounds of the formula:

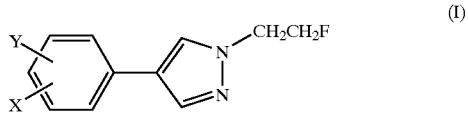

wherein X and Y are independently selected from the group consisting of hydrogen, halogen, alkyl, haloalkyl, nitro, alkylthio, alkylsulfinyl, alkylsulfonyl, and haloalkoxy. These compounds are useful as insecticides, nematocides, fungicides, and acaricides.

21 Claims, No Drawings

PESTICIDAL FLUOROETHYL PYRAZOLE DERIVATIVES

BACKGROUND OF THE INVENTION

1. Field of the Invention

The present invention relates to pesticidal fluoroethyl pyrazole derivatives. More particularly, this invention relates to fluoroethyl pyrazole derivatives that exhibit activity as insecticides, acaricides, fungicides, and nematocides. This invention also relates to insecticidal, acaricidal, fungicidal, and nematocidal compositions comprising the fluoroethyl pyrazole derivatives, and to methods of controlling insects, nematodes, fungi, and acarids using such compounds or compositions.

2. Description of Related Art

Destruction of crops by insects, acarids, fungi, and nematodes presents a serious problem to agriculture and a wide variety of field crops are in need of protection from them. Particularly difficult types of these pests to control are those which, at one or more stages of their life, inhabit the soil and cause destruction to the roots of plants. Accordingly, the development of fungicides and of insecticides, nematocides, and acaricides that are effective as ovicides, larvicides, and adulticides is desirable.

Baklouti and Hedhli, *Journal of Fluorine Chemistry* 45:255–263 (1989) (CA 112:198205), reported the preparation of certain fluoroethyl pyrazoles, but the 4-substitution of the instant invention was absent. In addition, they did not report biological properties of the compounds.

Japanese patent JP 59053468 1984 (CA 101:90922) refers to phenyl pyrazoles with fungicidal activity.

It is a purpose of this invention to provide novel fluoroethyl pyrazole derivatives and physiologically acceptable salts thereof that are useful as insecticides, nematocides, fungicides, and acaricides.

SUMMARY OF THE INVENTION

This invention relates to fluoroethyl pyrazole compounds of the formula:

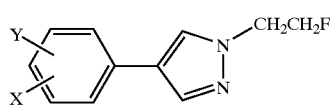

(I)

wherein X and Y are independently selected from the group consisting of hydrogen, halogen, alkyl, haloalkyl, nitro, alkylthio, alkylsulfinyl, alkylsulfonyl, and haloalkoxy. Where X and/or Y comprises an alkyl moiety, it is preferred that it be lower alkyl, e.g., alkyl of from 1 to 4 carbon atoms, such as, methyl, ethyl, propyl, butyl, or an isomer of the foregoing.

The compounds of the present invention are useful as plant protecting agents for the control of acarid, nematode, fungus, and insect pests. Thus, the present invention also relates to a pesticidal composition comprising: a) an effective amount of a compound of formula 1; and b) a suitable carrier. The present invention further relates to a method for controlling insects, nematodes, fungi, or acarids that comprises applying an effective amount of the compound of formula I to the locus to be protected.

More particularly, the present invention is directed to fluoroethyl pyrazole compounds of the formula:

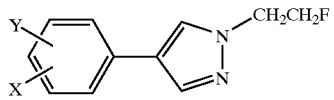

(I)

wherein X and Y are independently selected from the group consisting of hydrogen, halogen, alkyl, haloalkyl, nitro, alkylthio, alkylsulfinyl, alkylsulfonyl, and haloalkoxy.

In another aspect, the present invention is directed to a pesticidal composition comprising:

A) at least one fluoroethyl pyrazole compounds of the formula:

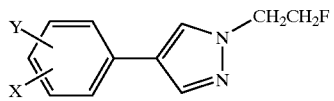

(I)

wherein X and Y are independently selected from the group consisting of hydrogen, halogen, alkly, haloalkyl, nitro, alkylthio, alkylsulfinyl, alkylsulfonyl, and haloalkoxy; and B) a suitable carrier.

In still another aspect, the present invention is directed to a method for controlling pests comprising applying an effective amount of at least one fluoroethyl pyrazole compound of the formula:

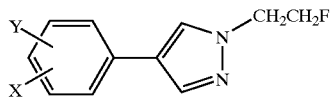

(I)

wherein X and Y are independently selected from the group consisting of hydrogen, halogen, alkyl, haloalkyl, nitro, alkylthio, alkylsulfinyl, alkylsulfonyl, and haloalkoxy, to the locus to be protected.

DESCRIPTION OF THE PREFERRED EMBODIMENTS

As stated above, the present invention is directed to fluoroethyl pyrazole compounds of the formula:

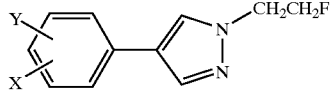

(I)

wherein X and Y are independently selected from the group consisting of hydrogen, halogen, alkyl, haloalkyl, nitro, alkylthio, alkylsulfinyl, alkylsulfonyl, and haloalkoxy. Preferably, where X and/or Y comprise an alkyl moiety, it is one of from 1 to 4 carbon atoms. Particularly preferred are the fluoroethyl pyrazole compounds of formula I wherein X and/or Y are hydrogen, halogen, haloalkyl, or haloalkoxy.

The compounds of the present invention can be prepared by reacting a substituted pyrazole with bromofluoroethane and an equivalent of a hydrogen halide, e.g.,HBr, acceptor, such as potassium carbonate or sodium hydride, in a solvent, such as acetonitrile or dimethylsulfoxide. Following the reaction, the product (I) is either precipitated by the addition of water or, if a liquid is formed, extracted into an organic solvent, such as diethyl ether or dichloromethane.

The following equation is illustrative of the process:

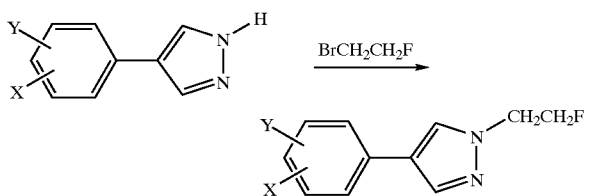

The present invention farther relates to a pesticidal composition comprising a) an effective amount of a fluoroethyl pyrazole derivative of formula I; and (b) a suitable carrier. Such suitable carriers may be solid or liquid in nature.

Suitable liquid carriers can comprise water, alcohols, ketones, phenols, toluene, and xylenes. In such formulations, additives conventionally employed in the art can be utilized, such as one or more surface active agents and/or inert diluents, to facilitate handling and application of the resulting insecticidal composition.

Alternatively, the compounds of this invention can be applied as a liquid or in sprays when utilized in a liquid carrier, such as a solution comprising a compatible solvent, such as acetone, benzene, toluene, or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the compound admixed therewith can be dispersed in water to form a suspension for application in such form.

Granular formulations of the compounds are preferred for field treatment and are suitable for application by broadcasting, side dressing, soil incorporation, or seed treatment, and are suitably prepared using a granular or pelletized form of carrier, such as granular clays, vermiculite, charcoal, or corn cobs. The compounds of this invention can be dissolved in a solvent and sprayed onto an inert mineral carrier, such as attapulgite granules (10–100 mesh), whereupon the solvent is evaporated. Such granular compositions can contain from 2–25% of a compound of this invention, based on carrier plus compound, preferably, 3–15%. In addition, the compounds of this invention can also be incorporated into a polymeric carrier, such as polyethylene, polypropylene, butadiene-styrene, styrene-acryonitrile resins, polyamides, poly(vinyl acetates), and the like. When encapsulated, the compounds of this invention can advantageously be released over an even longer time period, extending their effectiveness further than when used in non-encapsulated form.

Another method of applying the compounds of this invention to the loci to be treated is by aerosol treatment, for which the compounds can be dissolved in an aerosol carrier that is a liquid under pressure, but which is a gas at ordinary temperature (e.g., 20° C.) and atmospheric pressure. Aerosol formulations can also be prepared by first dissolving the compounds in a less volatile solvent and then admixing the resulting solution with a highly volatile liquid aerosol carrier.

For treatment of plants (such term including plant parts), the compounds of the invention preferably are applied in aqueous emulsions containing a surface-active dispersing agent, which can be non-ionic, cationic, or anionic. Suitable surface-active agents are well known in the art, such as those disclosed in U.S. Pat. No. 2,547,724 (columns 3 and 4).

The compounds of the present invention can be mixed with such surface-active dispersing agents, with or without an organic solvent, as concentrates for the subsequent addition of water, to yield aqueous suspensions of the compounds at desired concentration levels.

In addition, the compounds can be employed with carriers which themselves are pesticidally active, such as insecticides, acaricides, fungicides, or bactericides.

It will be understood that the effective amount of a compound in a given formulation will vary depending, e.g., upon the specific pest to be combated, as well as upon the specific chemical composition and formulation of the compound being employed, the method of applying the compound/formulation, and the locus of treatment. Generally, however, the effective amount of the compounds of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range from between about 0.01 and to about 50 pounds per acre, with concentrations of between about 0.1 and about 10 pounds per acre preferably being employed for crops such as corn, tobacco, rice, and the like.

To combat pests, sprays of the compounds can be applied to any suitable locus, such as to the pests directly and/or to plants upon which they feed or nest. The compositions of this invention can also be applied to the soil or other medium in which the pests are present.

The specific methods of application of the compounds and compositions of this invention, as well as the selection and concentration of these compounds, will vary depending upon such circumstances as crops to be protected, geographic area, climate, topography, plant tolerance, and the like.

The compounds of the invention are particularly useful as insecticides, nematocides, fungicides, and acaricides, for foliar and/or soil application. The compounds are particularly effective for controlling insects, such as corn rootworm, which live in the soil during one or more phases of their lives, by means of soil application.

The advantages and the important features of the present invention will be more apparent from the following examples.

EXAMPLES

Example 1

Preparation of 4-(2-fluoroethyl)-4-phenyl-1H-pyrazole (Compound 1)

To 2.0 grams of 4-phenyl-1H-pyrazole, 10 mL of dimethyl sulfoxide and 1.5 g of potassium carbonate were added and the solution was stirred at room temperature. Then, 1.5 grams of 1-bromo-2-fluoroethane was added dropwise. After addition of the bromofluoroethane, the mixture was stirred at room temperature for 24 hours, then poured into 100 mL of water. The precipitated product was filtered off, washed with water, and air-dried. There was obtained 2.0 grams of 4-(2-fluoroethyl)-4-phenyl-1H-pyrazole. The compounds summarized in Table 1 were prepared using essentially the same procedure as shown above. Each of the compounds so formed is characterized by its NMR characteristics.

TABLE 1

| Compound No. | X and/or Y | NMR Data (CDCl$_3$) |
|---|---|---|
| 1 | H | m(4) 4.1–5.3, m(7) 7.2–7.7 |
| 2 | 4-Cl | m(4) 4.1–5.3, m(6) 7.3–7.8 |
| 3 | 4-CF$_3$ | m(4) 4.1–5.3, m(6) 7.4–7.9 |
| 4 | 3-Br | m(4) 4.1–5.3, m(6) 7.4–7.9 |
| 5 | 3,4-Cl | m(4) 4.1–5.3, m(5) 7.3–7.9 |
| 6 | 3-CF$_3$ | m(4) 4.1–5.3, m(6) 7.3–7.8 |
| 7 | 4-OCF$_3$ | m(4) 4.1–5.3, m(6) 7.3–7.8 |

The remaining examples relate to the pesticidal use of the compounds of this invention.

Example 2

Stock Solution Preparation

Stock solutions of each of the compounds were prepared at 1000 ppm by dissolving 0.08 gram of each compound to be tested in 8 mL of acetone and adding 72 mL of distilled water plus 3 drops of ethoxylated sorbitan monolaurate, a wetting agent. These stock solutions were used in the remaining examples to demonstrate the pesticidal use of representative compounds of this invention. For each example that follows, these stock solutions were used and the specified dilutions made. All the tests discussed below, which involved treatment with compounds of this invention, were always repeated with controls to permit a comparison upon which the percent control was calculated.

Example 3

Mite Adulticide and Mite Ovicide Tests

One day before treatment of cowpea primary leaves with the test solutions, a "FIG. 8" configuration of tree tanglefoot was applied to each of two cowpea primary leaves, one from each of two plants in a pot. In each "Figure", the circle nearer the stem was designated for the mite ovicide test and the circle farther from the stem was designated for the mite adulticide test. Groups of adult mites (*Tefranychus urticae* Koch) were transferred into ovicide circles one day before treatment and the females were allowed to deposit eggs until one hour before treatment, at which point all the adults were removed. The plants were then sprayed to run off with each 1000 ppm stock solution of Example 2. One day following treatment of the plants with the test solution, groups of approximately 25 adult mites were transferred into the adulticide rings. Five days later, these rings were examined for live mites remaining on the leaves. The percent control was estimated based on the number of mites surviving on the control plants. Nine days following treatment the ovicide rings were examined for unhatched eggs and living immature mites. The percent control was estimated based on the number of unhatched eggs. Results of the mite adulticide (MI) and ovicide (MIOV) tests are presented in Table 2.

Example 4

Rice Planthopper Foliar Test

One thousand ppm of each stock solution of Example 2 was used for this test. One pot containing approximately 20 rice seedlings was treated with each formulation by spraying with a spray atomizer. One day after treatment, plants were covered with a tubular cage and 20 adult rice delphacids, *Sogatodes orizicola*, were transferred into each cage. Five days after transferring, counts were made of the surviving planthoppers in each pot and percent control was estimated. Results of the testing of rice planthoppers (RPH) are presented in Table 2.

Example 5

Tobacco Budworm Test

For each compound tested, 0.2 mL of each stock solution of Example 2 was pipetted onto the surfaces of each of five diet cells, allowed to spread over the surfaces, and air dried for two hours. Then, a second instar *Helicoverpa virescens* larva was introduced into each cell. After 14 days, the number of living larvae was determined for each treatment and percent control, corrected by Abbott's formula (*J. Econ. Entomology* (1925, 265–267), was calculated. The results of the testing of tobacco budworms (TB) are presented in Table 2.

Example 6

Southern Corn Rootworm Test

One thousand ppm of each stock solution of Example 2 was diluted to 100 ppm (the "test solution"). For each compound, 2.5 mL of each test solution was pipetted onto a filter paper (Whatman #3) at the bottom of a 100 mm petri dish. Two corn seedlings were soaked in the 100 ppm solution for one hour and transferred to the petri dish containing the same test solution. After 24 hours, each dish was loaded with 5 second instar larvae of Southern Corn Rootworm (*Diabrotica undecimpuncatat*). After five days, the number of live larvae was noted and the percent control, corrected by Abbott's formula, was calculated. The results of the testing of Southern Corn Rootworm (CR) are presented in Table 2.

Example 7

Nematode Test

One thousand ppm of each stock solution of Example 2 was used for this test. For each test solution, 25 mL was drenched onto separate 500 gram samples of soil infested with root knot nematode (*Meloidogmne incognita*) eggs in a pot, for a soil concentration of 50 ppm. One day after treatment, two tomato seedlings were planted in each pot. Nineteen days after planting, the roots were evaluated for the presence of knots or galls, and the percent control was estimated on the infestation levels in check plants. The results of the testing of nematodes (NE) are presented in Table 2.

TABLE 2

| Compound Number | Pesticidal Activity Percent Control | | | | | |
|---|---|---|---|---|---|---|
| | MI | MIOV | RPH | TB | CR | NE |
| 1 | 0 | 100 | 20 | 20 | 0 | 50 |
| 2 | 100 | 100 | 0 | 40 | 100 | 100 |
| 3 | 0 | 0 | 0 | 100 | 100 | 0 |
| 4 | 100 | 100 | 0 | 7 | 0 | 100 |

TABLE 2-continued

| Compound Number | Pesticidal Activity Percent Control | | | | | |
|---|---|---|---|---|---|---|
| | MI | MIOV | RPH | TB | CR | NE |
| 5 | 100 | 100 | 0 | 0 | 63 | 60 |
| 6 | 0 | 100 | 85 | 0 | 100 | 100 |
| 7 | 0 | 100 | 85 | 0 | 100 | 100 |

In view of the many changes and modifications that can be made without departing from principles underlying the invention, reference should be made to the appended claims for an understanding of the scope of the protection to be afforded the invention.

What is claimed is:

1. A fluoroethyl pyrazole compound of the formula:

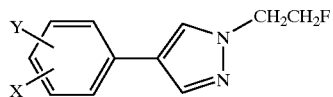
(I)

wherein X and Y are independently selected from the group consisting of hydrogen, halogen, alkyl, haloalkyl, nitro, alkylthio, alkylsulfinyl, alkylsulfonyl, and haloalkoxy.

2. The fluoroethyl pyrazole compound of claim 1 wherein X and Y are independently selected from the group consisting of hydrogen, halogen, haloalkyl, and haloalkoxy.

3. The fluoroethyl pyrazole compound of claim 2 wherein X and Y are both hydrogen.

4. The fluoroethyl pyrazole compound of claim 2 wherein X is hydrogen and Y is chloro.

5. The fluoroethyl pyrazole compound of claim 2 wherein X is hydrogen and Y is $CF_3$.

6. The fluoroethyl pyrazole compound of claim 2 wherein X is hydrogen and Y is bromo.

7. The fluoroethyl pyrazole compound of claim 2 wherein X is hydrogen and Y is $OCF_3$.

8. The fluoroethyl pyrazole compound of claim 2 wherein X and Y are both chloro.

9. A pesticidal composition comprising:
A) at least one fluoroethyl pyrazole compounds of the formula:

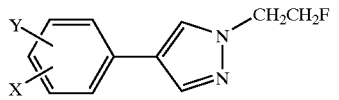
(I)

wherein X and Y are independently selected from the group consisting of hydrogen, halogen, alkyl, haloalkyl, nitro, alkylthio, alkylsulfinyl, alkylsulfonyl, and haloalkoxy; and
B) a suitable carrier.

10. The pesticidal composition compound of claim 9 wherein X and Y are independently selected from the group consisting of hydrogen, halogen, haloalkyl, and haloalkoxy.

11. The pesticidal composition compound of claim 10 wherein X and Y are both hydrogen.

12. The pesticidal composition compound of claim 10 wherein X is hydrogen and Y is chloro.

13. The pesticidal composition compound of claim 10 wherein X is hydrogen and Y is $CF_3$.

14. The pesticidal composition compound of claim 10 wherein X is hydrogen and Y is bromo.

15. The pesticidal composition compound of claim 10 wherein X is hydrogen and Y is $OCF_3$.

16. The pesticidal composition compound of claim 10 wherein X and Y are both chloro.

17. A method for controlling pests comprising applying an effective amount of at least one fluoroethyl pyrazole compound of the formula:

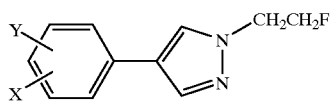
(I)

wherein X and Y are independently selected from the group consisting of hydrogen, halogen, alkyl, haloalkyl, nitro, alkylthio, alkylsulfinyl, alkylsulfonyl, and haloalkoxy, to the locus to be protected.

18. The method of claim 17 wherein the pest is an insect.

19. The method of claim 17 wherein the pest is an acarid.

20. The method of claim 17 wherein the pest is a nematode.

21. The method of claim 17 wherein the pest is a fungus.

* * * * *